US006918883B2

(12) United States Patent
Horton et al.

(10) Patent No.: US 6,918,883 B2
(45) Date of Patent: Jul. 19, 2005

(54) SOCK FOR DETECTION OF PRESSURE POINTS ON FEET

(75) Inventors: James M. Horton, Charlotte, NC (US); David Hinks, Apex, NC (US); Ahmed El-Shafei, Raleigh, NC (US)

(73) Assignee: Cannon Research Institute of Carolinas Medical Center, Charlotte, NC (US)

( * ) Notice: Subject to any disclaimer, the term of this patent is extended or adjusted under 35 U.S.C. 154(b) by 44 days.

(21) Appl. No.: 10/464,413

(22) Filed: Jun. 18, 2003

(65) Prior Publication Data

US 2004/0006286 A1 Jan. 8, 2004

Related U.S. Application Data

(63) Continuation-in-part of application No. 10/149,566, filed as application No. PCT/US00/33892 on Dec. 14, 2000, now Pat. No. 6,796,949.
(60) Provisional application No. 60/170,816, filed on Dec. 15, 1999.

(51) Int. Cl.[7] .............................................. A61B 5/103
(52) U.S. Cl. ..................... 600/592; 600/300; 600/587
(58) Field of Search ................................ 600/300, 587, 600/592; 2/239; 36/10, 83, 84, 98; 73/1.15, 862, 862.381, 147

(56) References Cited

U.S. PATENT DOCUMENTS

| | | | |
|---|---|---|---|
| 4,610,253 A | | 9/1986 | Rosenberg |
| 4,647,918 A | | 3/1987 | Goforth |
| 4,858,621 A | * | 8/1989 | Franks ........................ 600/592 |
| 4,905,383 A | | 3/1990 | Beckett et al. |
| 5,186,046 A | | 2/1993 | Gouterman et al. |
| 5,341,676 A | * | 8/1994 | Gouterman et al. .......... 73/147 |
| 5,390,680 A | | 2/1995 | Brenner |
| 5,546,955 A | | 8/1996 | Wilk |
| 5,566,479 A | | 10/1996 | Gray et al. |
| 5,612,492 A | | 3/1997 | Schwab et al. |
| 5,642,096 A | | 6/1997 | Leyerer et al. |
| 5,678,448 A | * | 10/1997 | Fullen et al. .................. 73/172 |
| 5,678,566 A | * | 10/1997 | Dribbon ..................... 600/592 |
| 5,775,332 A | * | 7/1998 | Goldman .................... 600/587 |
| 5,854,682 A | | 12/1998 | Gu |
| 5,918,317 A | | 7/1999 | Bernhardt |
| 5,957,870 A | * | 9/1999 | Yamato et al. ............... 600/592 |
| 5,965,642 A | | 10/1999 | Gouterman et al. |

FOREIGN PATENT DOCUMENTS

| | | |
|---|---|---|
| JP | 7076587 A | 3/1995 |
| JP | 8156430 A | 6/1996 |

OTHER PUBLICATIONS

Carroll, B., et al., "Step Response of Pressure–Sensitive Paints," *AIAA Journal*, 1996, vol. 34(3), pp. 521–526.
Gouin, S., et al., "Ideality of Pressure–Sensitive Paint. IV. Improvement of Luminescence Behavior by Addition of Pigment," *Journal of Applied Polymer Science*, 2000, vol. 77, pp. 2824–2831 John Wiley & Sons Inc.
Hampton, G., "Therapeutic Footwear for the Insensitive Foot," *Physical Therapy*, Jan. 1979, vol. 59(1), pp. 23–29.
Hubner, J., et al., "Application of Dual Sorption Theory to Pressure–Sensitive Paints," *AIAA Journal*, 1997, vol. 35(11), pp. 1790–1792.
Hughes, R., et al., "A Laser Plantar Pressure Sensor for the Diabetic Foot," *Medical Engineering & Physics*, 2000, vol. 22, pp. 149–154, Elsevier Science Ltd.
Kavandi, J., et al., "Luminescent Barometry in Wind Tunnels," *Rev. Sci. Instrum.*, Nov. 1990, vol. 61(11), pp. 3340–3347, American Institute of Physics.
Pauly, S., "Permeability and Diffusion Data," *Polymer Handbook*, 1989, pp. 435–449, 3$^{rd}$ ed., John Wiley & Sons, Inc.
Peterson, J., et al., "New Technique of Surface Flow Visualization Based on Oxygen Quenching of Fluorescence," *Rev. Sci. Instrum.*, May 1980, vol. 51(5), pp. 670–671, American Institute of Physics.
Rajeswaramma, V., et al., "Pressure–Sensitive Stump Sock," *Archives of Physical Medicine and Rehabilitation*, Mar. 1973, pp. 142–144.
Van Acker, K., et al., "Cost and Resource Utilization for Prevention and Treatment of Foot Lesions in a Diabetic Foot Clinic in Belgium," *Diabetes Res. Clin. Pract.*, 2000, vol. 50(2), pp. 87–95.

* cited by examiner

*Primary Examiner*—Robert L. Nasser
*Assistant Examiner*—Patricia C. Mallari
(74) *Attorney, Agent, or Firm*—Alston & Bird LLP

(57) ABSTRACT

The present invention provides a sock containing a coating applied to at least a portion of a surface of the sock for sensing pressure points on a patient's foot. The coating material comprises a pressure-sensitive film comprised of oxygen-sensitive photo luminescent probe molecules dispersed within a polymer matrix, and, optionally, an inorganic pigment. Areas of increased pressure can be detected by correspondence to areas on the film of increased fluorescence intensity. The coating material can also be comprised of a coloring agent or dye such that after the sock has been worn for a period of time, in those areas of the foot susceptible to pressure points, the coating material transfers from the interior of the sock and adheres to the foot in those points. The present invention is particularly applicable to persons having diabetic neuropathic feet wherein portions of the foot may be insensitive to pressure.

34 Claims, No Drawings

SOCK FOR DETECTION OF PRESSURE POINTS ON FEET

CROSS-REFERENCE TO RELATED APPLICATIONS

This application is a Continuation-in-Part of application Ser. No. 10/149,566, filed Oct. 7, 2002 now U.S. Pat. No. 6,796,949, which is a 35 U.S.C. §371 National Stage Commencement of Application Ser. No. PCT/US00/33892, filed Dec. 14, 2000, which claims the benefit of priority of Provisional Application Ser. No. 60/170,816, filed Dec. 15, 1999, all of which are incorporated herein by reference in their entirety.

FIELD OF THE INVENTION

The present invention relates to a sock having means for the detection of pressure points on a foot of a patient having diminished sensation in the foot and to a method for sensing diabetic neuropathic foot disease. The present invention further relates to a pressure-sensitive film and the use of the film for detecting pressure distribution across a surface, particularly on the foot of a patient. More specifically, the present invention relates to a sock having a pressure-sensitive film or a coloring agent or dye applied thereto that is useful for detecting pressure points on the foot of a patient having diminished sensation in the foot.

BACKGROUND OF THE INVENTION

Approximately 17 million people in the United States, or 6.2% of the population, have diabetes. Diabetes is a disease in which the body does not produce or properly use insulin, a hormone that is necessary to maintain blood sugar concentration at normal levels. When insulin is not produced or properly used by the body, glucose remains in the bloodstream instead of being shuttled into cells for energy production, resulting in high blood glucose, or high "blood sugar" levels.

High blood sugar can manifest its presence through multiple symptoms, including, increased thirst, frequent urination, weight loss, increased hunger, blurred vision, irritability, tingling or numbness in the hands or feet, frequent skin, bladder, or gum infections, wounds that don't heal, and extreme, unexplained fatigue. If left untreated, diabetes can lead to death, and even diabetics undergoing doctor-supervised treatment suffer an increased death rate as compared to the average population. In 1999, approximately 450,000 deaths occurred among people with diabetes aged 25 years and older. This figure represents about 19% of all deaths in the United States in people aged 25 years and older. Overall, the risk for death among people with diabetes is about 2 times that of people without diabetes. However, the increased risk associated with diabetes is greater for younger people (3.6 times for people aged 25–44 years versus 1.5 for those aged 65–74 years) and women (2.7 times for women aged 45–64 years versus 2.0 for men in that age group).

Diabetics also face risk of multiple complications during their lifetime arising from the disease. Some of the more serious complications include: heart disease (the leading cause of death in diabetics); stroke (risk of stroke is 2 to 4 times greater for diabetics); high blood pressure (about 73% of diabetics); blindness (diabetic retinopathy causes 12,000 to 24,000 new cases each year and diabetes is the leading cause of new cases of blindness among adults 20–74 years old); kidney disease (diabetes is the leading cause of treated end stage renal disease, accounting for 43% of new cases); nervous system disease (60–70% of diabetics have mild to severe damage, such as impaired sensation of pain in the feet or hands, slowed digestion, and carpal tunnel syndrome); dental disease (almost one-third of diabetics have severe periodontal diseases); pregnancy complications (poorly controlled diabetes before conception and during the first trimester of pregnancy can cause major birth defects in 5–10% of pregnancies and spontaneous abortions in 15–20% of pregnancies); and amputations (more than 60% of non-traumatic lower-limb amputations in the United States occur among diabetics).

Diabetic neuropathic foot disease is the most common cause of amputation in the United States and arises due to coordination of several of the complications listed above. These complications often stem from the disturbance of the body's metabolism caused by the prolonged high blood sugar. The disturbance includes increased levels of serum cholesterol, triglycerides, and glucosylated hemoglobin, which lead to precipitation of the substances on the inner lining of the small blood vessels (especially capillaries) everywhere in the body, and more so in terminal blood vessels, like those found in the legs and feet. This precipitation then leads to stenosis of the blood vessels, ultimately resulting in a condition termed diabetic microangiopathy, or literally, disease of the capillaries related to diabetes. Long-standing stenosis that is widespread may decrease the total capacity of blood circulation within the body, which contributes to the high blood pressure condition referenced above. The most dangerous effect of microangiopathy, especially in the lower limbs, is occurrence of ischaemia (decreased blood supply) in the foot and leg. This condition can progress with inadequate supply of oxygen and nutrients, eventually producing devitalization and change of texture and color of the foot, starting with the big toe, which can then spread to the rest of the limb in a process called gangrene.

Diabetic patients also have increased risk of complications associated with their lower extremities, especially the feet, due to nervous system disease, as described above, that can lead to a partial or complete loss of feeling. A healthy person that starts to feel pain when subjected to continuous local pressure may shift their body or make other suitable alterations to automatically lessen the discomfort; however, patients having a sensory loss are deprived of this protection and are therefore common victims of pressure sores and open wounds that can become ulcerated. It is therefore desirable to detect the pressure points in the foot to prevent pressure sores and wounds so that a patient who might not be able to recognize existence of a pressure point inducing condition can take curative or preventative measures to eliminate or reduce the condition.

The development of protocols capable of diagnosing potential areas for the development of plantar ulcers would be of great value in decreasing and preventing diabetic foot amputation. Diabetic foot lesions are an underlying cause of hospitalization, disability, morbidity, and mortality, especially among elderly people. A protocol for early detection of plantar ulceration would avoid the need for follow-up examinations, supplementary examinations, local wound debridement, orthopedic appliances, and in some critical cases frequent hospitalization, and amputation. According to one study, it was estimated that the average cost per case of preventative care is $880, while the average cost per case for curative care is $5,227, and the average cost per case for severe lesions and amputation is $31,716 (See Van Acker, K. et al., "Cost and Resource Utilization for Prevention and Treatment of Foot Lesions in a Diabetic Foot Clinic in Belgium" Diabetic Research and Clinical Practice, 50:87–95 (2000)).

Devices are known in the prior art for indicating to persons having diminished sensation in the foot that their feet are being exposed to excessive stress conditions that could possibly lead to plantar ulcers or worse. Many of these devices include shoes, which detect excess pressure through a force sensor and signals the wearer of the existence that a threshold pressure has been reached. Examples of such devices are described in U.S. Pat. No. 5,566,479, U.S. Pat. No. 4,610,253, U.S. Pat. No. 4,647,918, and U.S. Pat. No. 5,642,096. The difficulty with such devices is that they are expensive and cumbersome to wear. Accordingly, it is desirable that there be provided a method for conveniently detecting the pressure points in the foot of a patient with diminished sensation.

A study was recently performed using interferometry for detecting plantar pressure distribution involving a laser light oriented towards a compressed plate (See Hughes, R. et al., "A Laser Plantar Pressure Sensor for the Diabetic Foot" *Medical Engineering and Physics,* 22:149–154 (2000)). This approach involves a pressure plate, which compresses when subjected to a load. The interferogram produced represents the pattern of pressure distribution across the plate. Such approaches as this pose an improvement over the cumbersome, expensive footwear noted above, but this method still suffers from drawbacks, such as ease of use, mass availability, and expense. Further, such methods are only useful for analyzing the bottom or sole of the foot and fails to account for pressure points on other parts of the foot. Therefore, there still remains a need for a method for detecting pressure points, especially in the foot of a patient with diminished sensation, that is effective, easy to apply, and relatively cost-effective.

BRIEF SUMMARY OF THE INVENTION

An object of the present invention is to provide a sock having means for the detection of pressure points on a foot of a patient having diminished sensation in the foot.

Another object of the present invention is to provide a sock containing a dye which, when the sock is worn, at least a portion of the dye is transferred from the sock and adheres to pressure points of a patient's foot.

Yet another object of the present invention is to provide a sock containing a pressure-sensitive film applied to at least a portion of the inner or outer surface of the sock being useful for detecting pressure distribution across the surface of the foot.

Yet another object of the present invention is to provide a method for sensing neuropathic foot disease.

The present invention provides a sock for detecting pressure points on a foot wherein the sock comprises a sock containing a pressure-sensitive film applied to at least a portion of the sock. The film comprises an oxygen permeable polymer matrix, oxygen-sensitive photo luminescent probe molecules dispersed within the matrix, and, optionally, at least one inorganic pigment.

In another aspect of the present invention is provided a method for diagnosing potential areas for the development of plantar ulcers. The method comprises providing a pressure-sensitive film comprising an oxygen permeable polymer matrix, oxygen-sensitive photo luminescent probe molecules dispersed within the matrix, and, optionally, at least one inorganic pigment, for detecting pressure distribution across a surface when subjected to a load, subjecting the surface of the film to foot pressure exerted by a patient, exposing the film to a light source capable of exciting the probe molecules from the ground energy state to an excited energy state, detecting the energy released by the probe molecules when they return from the excited energy state to the ground energy state, and determining the areas where the foot exerted the greatest pressure on the surface of the film by comparing a map of the emission spectra with the film and the patient's foot.

In still another aspect of the present invention is provided a method for detecting pressure points on a foot of a patient. The method comprises providing a sock having an inner and an outer surface with a pressure-sensitive film comprising an oxygen permeable polymer matrix, oxygen-sensitive photo luminescent probe molecules dispersed within the matrix, and, optionally, at least one inorganic pigment, applied to at least a portion of the inner or outer surface of the sock, fitting the sock to the foot of a patient, wearing the sock for a period of time, exposing the sock to a light source capable of exciting the probe molecules from the ground energy state to an excited energy state, detecting the energy released by the probe molecules when they return from the excited energy state to the ground energy state, and determining the areas where the foot exerted the greatest pressure on the sock by comparing a map of the emission spectra with the film and the patient's foot.

According to another aspect of the present invention, there is provided a sock for detecting pressure points on a foot of a patient being diagnosed for diminished sensation in the foot. The sock has a coating material applied to at least a portion of the interior surface of the sock so that when the patient wears the sock, the coating material transfers from the interior surface of the sock to the foot at the pressure points.

According to still another aspect of the present invention, a method is provided for detecting pressure points on a foot of a patient being diagnosed for diminished sensation in the foot. The method includes fitting a sock having a removable coating material applied to at least a portion of the interior of the sock to the foot to be examined, having the patient wear the sock for a period of time, and removing the sock to determine the points of the foot where the removable coating material has been transferred to the foot.

The present invention is useful for any patient experiencing sensory neuropathy, and it is particularly useful for diabetes patients. The sock of this invention can be worn with shoes on. Thus the patient can perform normal activities while pressure points can be detected in real time. Once the pressure points in the patient's feet are detected, the patient may then be treated to prevent the development of sores or ulcers. Conventionally, the patient's shoes can be altered to ease the pressure in the affected portion of the foot.

Further features and advantages of the invention will be apparent from the description below.

DETAILED DESCRIPTION OF THE INVENTION

The present invention now will be described more fully hereinafter with reference to preferred embodiments of the invention. This invention may, however, be embodied in many different forms and should not be construed as limited to the embodiments set forth herein; rather, these embodiments are provided so that this disclosure will be thorough and complete, and will fully convey the scope of the invention to those skilled in the art.

The present invention provides a sock for detecting pressure points on a foot. The sock is normally sized to substantially conform to the shape of a human foot and comprises a sock containing a pressure-sensitive film or coloring agent or dye applied to at least a portion of the sock. Where a coloring agent or dye is used, the sock will generally have a sufficiently snug fit to allow transfer of the coloring agent or dye to a pressure point. Where a pressure-sensitive film is used, the sock will generally have a sufficiently snug fit to allow a pressure distribution across the film that is in accord with a pressure point. Pressure-sensitive paints (PSP), or pressure-sensitive films, have been previously described and typically comprise oxygen-sensitive photo luminescent molecules dissolved in a silicone resin polymer matrix (Kavandi et al., "Luminescent Barometry in Wind Tunnels" *Rev. Sci. Instrum.* 61(11):3340–3347 (1990)). The luminescence of the molecules is limited in that it is quenched through interaction with oxygen molecules, meaning that an increase in amount of molecular oxygen present in the silicone polymer matrix leads to a decrease in the intensity of the luminescence.

The term "pressure-sensitive-paint" or "PSP" and the term "pressure-sensitive film" are meant to be interchangeable as used throughout this description. All paints or paint-like materials, when applied to a surface, can be viewed, in a generic sense, as forming a film over the surface when dry. Further, the term "film" is generally defined as being a thin layer or coating, or a thin sheet of any material. Thus, the term "film," as used in relation to the present invention, is intended to encompass a pressure-sensitive paint that has been applied to a surface and allowed to cure such that when physical contact is made between a secondary object and the pressure-sensitive film, the film remains bound to the surface and does not adhere to the secondary object. The use of the term "film" is not intended to impart any limitation in regard to the thickness of the PSP coating. Rather, it is only intended to be descriptive in regard to the PSP being in a substantially solid state as opposed to a substantially liquid state.

The active ingredient in a PSP is the photo luminescent molecule, which is typically an organic compound that luminesces (gives off energy in the form of photons, or light) when exposed to light of a specific wavelength. A PSP is "pressure-sensitive" in that the emitted photons are susceptible to quenching, which describes the phenomenon of the PSP atomic particles interacting with other molecules in a manner that results in the loss of the excitation energy without the normally resulting photon (or light) emission. A quenching agent normally associated with a PSP is oxygen.

Any photo luminescent molecule that luminesces when exposed to a light source and is susceptible to oxygen quenching can be used in the present invention. A group of compounds that is particularly useful as the photoluminescent material in the present invention is the porphyrins. Porphyrins are a group of compounds based on the structure of the parent compound, porphine, shown below in formula I.

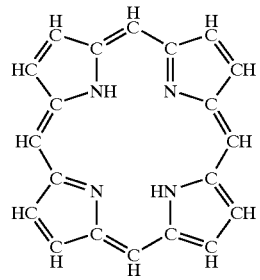

(I)

The parent compound, porphine, is comprised of four pyrrole rings (which are weakly aromatic) and are joined by methene bridges. Other members of the porphyrin family are formed through the substitution of side chains for the hydrogen substituents in the pyrrole rings.

Examples of photo luminescent molecules that are useful in the present invention include platinum octaethylporphyrin (PtOEP), palladium octaethylporphyrin (PdOEP), platinum tetra(pentafluorophenyl)porphyrin (PtTFPP), palladium tetra(pentafluorophenyl)porphyrin (PdTFPP), platinum tetraphenylporphyrin (PtTPP), palladium tetraphenylporphyrin (PdTPP), platinum octaethylporphyrin ketone (PtOEPK), palladium octaethylporphyrin ketone (PdOEPK), platinum tetrabenzoporphyrin (PtTBP), palladium tetrabenzoporphyrin (PdTBP), and tris(2,2'-bipyridine)ruthenium(II) chloride pentahydrate. Additional photo luminescent molecules that are useful in the present invention are complexes of ruthenium (II), osmium (II), iridium (III), rhodium, rhenium, or chromium (III) with 2,2'-bipyridine, 1,10-phenanthroline, 4,7-diphenyl(1,10-phenanthroline), 4,7-dimethyl-1,10-phenanthroline, 4,7-disulfonated-diphenyl-1,10-phenanthroline, 2,2'-bi-2-thiazoline, 2,2'-bithiazole, 5-bromo-1,10-phenanthroline, or 5-chloro-1,10-phenanthroline. A preferred photo luminescent molecule for use in the present invention is platinum octaethylporphyrin (PtOEP).

In addition to the photo luminescent active ingredient, the PSPs useful in the present invention also comprise a binder in which the photo luminescent molecules are bound. Such binding can be a suspension, dispersion, solution, or any other mixture wherein the photo luminescent molecules can be contained within the binder such that each active molecule is surrounded by the binder molecules. Various binders are known in the art, and the choice of binder can be determined by the proposed application of the PSP. For example, U.S. Pat. No. 5,612,492 discloses the use of silanol-terminated polydimethylsiloxane as a PSP binder with high oxygen permeability. The characteristic of high oxygen permeability is highly important in determining the effectiveness of a binder material because oxygen must be allowed to permeate the PSP in order for the oxygen quenching phenomenon to be applicable. While silicon based materials are often used as the binder for PSPs, other materials have also been shown effective as a PSP binder. For example, U.S. Pat. No. 5,965,642 describes the use of acrylic or fluoroacrylic polymers as a binder material. Preferred binders for use in the present invention include polydimethylsiloxane and methyltriacetoxysilane.

The usefulness of a PSP is based upon the oxygen quenching phenomenon to which some photo luminescent molecules are susceptible. When a photo luminescent molecule is subjected to specific frequencies of light it will absorb energy, placing the molecule in an excited state. As the molecule is less stable at the excited state, it returns to its ground state by releasing the energy in the form of a photon. The released energy (also known as the emission energy) generally manifests itself in the form of irradiation, such as light, that is at a longer wavelength than that of the originally absorbed light (also known as the excitation energy). If the wavelength of the emitted photon (also known as the emission spectra) is in the visible spectrum, the release of energy is seen visually as light, or luminescence. For some luminescent molecules, however, the luminescence is quenched by the presence of oxygen molecules, which absorb the emitted energy before it can be detected visually as luminescence. Therefore, for a given level of excitation, the emitted light intensity from the luminescent molecules varies inversely with the local oxygen partial pressure. Since the mole fraction of oxygen in the air is fixed, the oxygen partial pressure is easily converted into the air pressure. This relationship between luminescent intensity and air pressure has been used advantageously in wind tunnel barometry. For example, U.S. Pat. No. 5,612,492 teaches that PSPs can be applied to aerodynamic surfaces to be used in wind-tunnel pressure testing. The oxygen sensitivity of the luminescent molecules is also a characteristic of the PSP that makes it useful in the present invention.

In one aspect of the present invention, a sock is provided for detecting pressure points on a patient's foot. The sock can be described as having an inner, or interior, and an outer, or exterior, surface, wherein the inner surface is understood to be the surface of the sock that is in physical contact with the foot, and wherein the outer surface of the sock is understood to the surface of the sock that is not normally in actual, physical contact with the foot (i.e., is susceptible to contact with its surroundings, such as, for example, a shoe). For purposes of clarity, particularly in reference to the sock surfaces, the term "inner" is intended to by interchangeable with the term "interior", and the term "outer" is intended to be interchangeable with the term "exterior". In one embodiment, at least a portion of at least one of the inner and outer surfaces of the sock is coated with a pressure sensitive paint. The pressure-sensitive paint can be applied to any portion of the sock such that when worn by the patient, the pressure-sensitive paint will be on a portion of the sock that corresponds to an area on the foot of the patient that is a possible pressure point.

The PSP applied to the sock is allowed to cure, or dry, prior to use. The cured PSP can be referred to as a pressure-sensitive film. The terms, however, are interchangeable. The sock with the pressure-sensitive film can be worn by a patient to determine which areas of the foot are being subjected to excessive pressure. By "excessive" is meant pressure that is sufficiently high so as to adversely affect the pressure points, i.e., the locations on the foot withstanding the pressure. Examples of adverse effects could include causing sores or ulcerations. While it would normally be envisioned that the pressure points would be on the bottom or sole of the foot, the present invention also encompasses situations where the pressure points are on the top or side portions of the foot or the ankle area. Examples of such situations would include improperly fitted shoes imparting excessive pressure in the form of consistent pressure or rubbing of the area.

The pressure-sensitive paint to be applied to the sock of the present invention comprises photo luminescent molecules dissolved in a polymer matrix binder. The photo luminescent molecules may comprise any compound that is known to exhibit luminescence when exposed to a light source of a particular wavelength and is also known to be susceptible to quenching of the luminescence by oxygen molecules. Such compounds may be referred to as oxygen-sensitive photo luminescent compounds. Exemplary oxygen-sensitive photo luminescent molecules that are useful in the present invention include each of the examples of photo luminescent molecules described earlier.

The pressure-sensitive paint of the present invention further comprises a binder, or polymer matrix. The polymer matrix is preferably comprised of a material exhibiting good diffusion properties. By good diffusion properties is meant a material exhibiting high gas permeability, especially in reference to oxygen. As previously stated, it is the oxygen-sensitivity of the photo luminescent molecules that makes them useful for PSPs. Therefore, it is necessary that the binder used in the PSP be a material or mixture of materials that exhibits an increased ability to allow oxygen to readily diffuse into and out of the matrix. Furthermore, the matrix should not exhibit a tendency to incorporate oxygen into the molecular structure of the matrix or to tightly bind the oxygen within the matrix. Rather, the polymer matrix should be capable of allowing oxygen molecules to freely diffuse throughout the matrix and should have a structural capacity such that oxygen molecules may freely diffuse away from areas where the matrix is compressed due to an applied force and into areas that are subject to less or no added pressure.

As stated above in the general description of pressure-sensitive paints, various types of materials have previously been shown to be useful as a binder or polymer matrix. It is preferred that the polymer matrix of the present invention be comprised of a material with the diffusional characteristics described above and be available at a low cost. It has been found that certain silicone polymers are both inexpensive and oxygen-permeable. Therefore, preferred materials for use as a polymer matrix in the present invention include silicone-based polymers and siloxane-based polymers. By "siloxane" is meant compounds having the structural unit $R_2SiO$, where R is an organic group or hydrogen. Most preferred for use as the polymer matrix of the present invention is polydimethylsiloxane. Other materials exhibiting the characteristics described above for use as a polymer matrix, which can be readily envisioned by one skilled in the art, are also contemplated by the present invention.

The interrelationship between the polymer matrix and the photo luminescent molecules plays an important role in the proper and useful function of the PSP. As previously stated, the polymer matrix must exhibit good diffusional characteristics. The diffusional characteristics are in turn a function of the activation energy of the oxygen molecules in the polymer matrix. As the photo luminescent molecules are susceptible to oxygen quenching, there is, therefore, a relationship between oxygen concentration and luminescence, which in turn is related to pressure exerted upon the pressure-sensitive film. In other words, areas within the film with a high oxygen concentration will experience high levels of oxygen quenching of the luminescence, and areas of the film with low oxygen concentration will experience low levels of oxygen quenching of the luminescence. Furthermore, oxygen levels within the film are subject to change as the result of the application of pressure upon the film. Therefore, when a pressure distribution is applied across the film, areas of higher pressure will result in areas of lower oxygen concentration, which equates to luminescence of greater intensity. The opposite is true for areas of lower pressure, where there will be higher oxygen concentration, meaning more quenching and lower luminescence intensity.

In a preferred embodiment of the present invention, the PSP is applied to at least a portion of the inner or outer surface of a sock and is comprised of a platinum octaethylporphyrin dissolved in polydimethylsiloxane.

When used in its generally accepted sense, the word "sock" is commonly held to refer to a knitted or woven covering for the foot, sometimes extending up a portion of the lower leg. Other accepted meanings for sock encompass a lightweight shoe or slipper. The word "sock" as used throughout herein is not intended to be limited to such conventional definitions but rather is intended to encompass any structure capable of covering the foot of a patient and substantially conforming to the shape of the patient's foot in a manner that would not substantially interfere with the patient's ability to function normally, including walking, for at least a short period of time. Exemplary types of socks useful in the present invention include, but are not limited to, conventional socks made of any textile or non-textile material, slippers, shoes, adhesive wraps, non-adhesive wraps, and other footwear that could readily be envisioned by one skilled in the art.

In one embodiment of the present invention, a PSP as described above comprising photo luminescent molecules dispersed within a polymer matrix is applied to at least a portion of the inner surface of a sock. A patient is then allowed to wear the sock for a period of time under conditions that are consistent with the patient's normal activities whereby pressure could be applied to the portion of the sock being coated by the PSP (i.e., the portion of the sock containing the pressure-sensitive film). After exposing the PSP-coated sock to the foot-pressure effect, an illumination device emitting excitation energy described by wavelength $\lambda_e$ and intensity $I_e$ is used to excite the probe molecules (i.e., the photo luminescent molecules) from the normal ground energy state to the excited energy state. As the excited energy state is less stable than the ground energy state, the molecules will readily release the excitation energy gained from the light source and return to the ground state. As the probe molecules return to the ground state, they will luminesce at a wavelength $\lambda$, which is less than $\lambda_e$, and intensity I, or they will lose the energy through oxygen quenching. The excitation energy necessary to excite the probe molecules will vary based upon the probe molecule used. Commonly used probe molecules, such as those described above, generally require an excitation source exhibiting a wavelength of about 200 nm to about 600 nm. The preferred probe molecule of the present invention, platinum octaethylporphyrin, requires an excitation energy source exhibiting a wavelength of about 450 nm to about 500 nm, preferably about 470 nm to about 480 nm. It is preferred that the required excitation energy be of a sufficiently large wavelength (and thus a sufficiently low frequency) such that exposing a patient to the excitation energy would not be harmful.

The illumination device of the present invention can be any light source capable of producing an excitation spectra that encompasses the wavelength necessary to excite the probe molecules from the ground state to the excited state. Further, since the intensity of the emitted energy is proportional to the excitation energy, the source of illumination must be of sufficient power in the absorption spectrum of the PSP coating, and also have a stable output over time. Some examples of illumination elements are lasers, continuous and flash arc lamps, and simple incandescent lamps. In a particularly preferred embodiment, the excitation source is an ultraviolet light source providing an excitation spectra in the UV range, especially the near UV range. It would be well known to one of skill in the art that by near UV range is meant a spectra in the wavelength range of about 200 nm to about 400 nm. Especially preferred according to the present invention is an excitation spectra of about 390 nm.

The emission spectra from the pressure-sensitive film can be detected and quantified through use of an imaging device capable of detecting radiation that includes the emission spectra of the photo luminescent molecules. Imaging devices capable of providing good spatial resolution are preferred and include, for example, conventional still photography, low-light video cameras, or scientific grade charge-coupled device (CCD) cameras. Preferred imaging devices are electronic CCD cameras due to their good spatial resolution and capability to reduce the data they acquire in real time. CCD cameras can be divided into two groups, conventional black and white video cameras and scientific grade CCD digital cameras. Conventional black and white cameras, while providing low cost, are less effective as they mainly offer only qualitative analysis. Scientific grade cooled CCD digital cameras, on the other hand, are precision scientific instruments that provide high-precision measurements. Typical cameras of this type can exhibit 16-bit intensity resolution and spatial resolution up to 2048×2048 pixels. One example of a device useful in the present invention for detecting and recording the emission spectra is a cooled, 14-bit CCD camera.

In order to avoid erroneous illumination readings, it is preferred that the illumination device only output in the absorption spectrum of the PSP, while the imaging or detecting device only records the emission spectrum. When lasers are used for excitation purposes, this is not an issue, as a laser only produces light in one wavelength. Most excitation sources, however, produce light in a wide spectrum. In order to prevent the excitation source spectrum from overlapping the emission spectrum, optical filters can be placed over the illumination device and the imaging device.

Once the emission spectrum has been analyzed, it can be used to determine the areas of the foot where the most pressure was exerted. This can be accomplished by comparing a map of the emission spectra to the sock and determining which areas on the sock correspond to the areas on the spectra that recorded the highest luminescence. The areas of highest luminescence will indicate the areas of the pressure-sensitive film that maintained the lowest oxygen concentrations and thus the least oxygen quenching. Accordingly, the areas of highest luminescence will correspond to the pressure points on the foot. Once these areas of highest luminescence are indicated on the sock, the emission spectra map can be compared against the foot to determine the areas on the foot that correspond to the areas of highest luminescence on the sock. In this manner, it is possible to determine the areas of the foot subjected to the most pressure.

In another embodiment of the present invention, the PSP includes an inorganic pigment. The luminescence in pressure-sensitive paints is limited by temperature dependence, wherein the intensity of the luminescence of the PSP under a given pressure can vary based upon the temperature of the PSP. Errors induced by the temperature change are small, but they can become more substantial where luminescence intensity changes due to pressure variations are small (See Gouin, S. and Gouterman, M., "Ideality of Pressure-Sensitive Paint. IV. Improvement of Luminescence Behavior by Addition of Pigment" *Journal of Applied Polymer Science* 77:2824–2831(2000)). One method for overcoming the temperature dependence is through the addition of an inorganic pigment, which functions to enhance diffusability inside the polymer matrix. The inorganic pigment has a significant role in affecting the activation energy of oxygen diffusion inside the polymer matrix, which is utilized to modify the temperature dependence of luminescence in the PSP. Temperature dependence could thus be controlled by the amount of pigment added to the PSP, making it possible to prepare a PSP formulation that is completely independent of temperature, or one that functions optimally under a specific temperature range, such as, for example, temperatures near or slightly higher than normal bodily temperatures. The diffusion properties in the polymer matrix are independent of the nature of the inorganic pigment used and are affected only by the pigment volume concentration (PVC). PVC is a measure of the pigment concentration in the dry coating and is defined by the following equation:

$$PVC = \frac{m_{pigment}/\rho_{pigment}}{(m_{pigment}/\rho_{pigment}) + (m_{binder}/\rho_{binder})}$$

wherein m is mass and $\rho$ is density in g/cm$^3$.

It can become more or less desirable to modify the temperature dependence based upon the method of use of the PSP. For example, in one embodiment of the present invention, it is envisioned that the patient could wear the sock with the pressure-sensitive film covering at least a portion of the inner or outer surface with no additional foot covering for a short period of time, such as approximately 10 to 30 minutes. In this embodiment, it would be expected that the sock, including the pressure-sensitive film, would be at a temperature very close to or less than normal bodily temperature. In another embodiment of the invention, it is envisioned that the patient could wear the sock with the pressure-sensitive film covering at least a portion of the inner or outer surface while also wearing an additional foot covering, such as, for example, a shoe or boot. Furthermore, according to this embodiment, the sock can be worn for a more extended period of time, such as, for example, 1 to 2 hours or more, to more closely approximate normal, everyday pressure the patient's foot would encounter. It would be expected that in this embodiment, the temperature of the pressure-sensitive film on the sock inside the shoe or boot would be at a temperature that is somewhat higher than normal bodily temperatures. Thus, it would be beneficial to have a PSP formulation capable of providing standardizable results across the two embodiments that is independent of the temperature variations.

Non-limiting examples of inorganic pigments that can be useful in lessening temperature dependence in the PSP of the present invention include aluminum oxide, iron oxide, lead oxide, chrome oxide, zinc phosphate, titanium dioxide, cadmium, ultramarine, zinc sulfide, barium sulfate, molybdate, and mixtures thereof. Preferred inorganic pigments for use in the present invention are aluminum oxide ($Al_2O_3$) and titanium dioxide ($TiO_2$). Most preferred, due to its superior photostability, is aluminum oxide.

The PSP is applied to a sock, or other device, and allowed to dry prior to having contact with the foot of the patient. The resultant pressure-sensitive film is not expected to have any adverse effects upon the patient caused by direct contact with the skin of the patient's foot or elsewhere. Thus, the pressure-sensitive film of the present invention can cover at least a portion of the inside of a sock and safely be worn by the patient for an extended period of time. However, for patients with unusually high sensitivities, such as to chemical mixtures, the present invention also contemplates applying the pressure-sensitive film to the outer surface of a sock so as to avoid direct contact of the film with the skin of the patient. Furthermore, the pressure-sensitive film can be applied to another device, such as the interior surface of a shoe, a shoe insole, or a device that is not worn by the patient. In this embodiment, the patient, wearing a sock or other foot covering that does not contain a pressure-sensitive film, can make use of the device that does include the pressure-sensitive film while further limiting contact of the film to the skin of the patient.

The PSP coating can be applied to the surface of the device by any suitable methods. For example, it can be applied as a spray and then allowed to dry. The polymer matrix, with the photo luminescent probe molecules suspended therein, can be made into a slurry in a suitable solvent, such as absolute ethanol or 1,1,1-trichloroethane. The device can then be spray-coated with the PSP and the solvent allowed to evaporate.

The sock, having at least a portion thereof covered with the pressure-sensitive film, can be used according to various methods, many of which would be readily apparent to one skilled in the art. In one embodiment of the present invention, the patient can wear the sock alone under normal walking conditions for a short period of time, such as between about 10 to about 30 minutes. According to another embodiment, the patient can wear the sock while also wearing the patient's own shoe to better simulate the types of external pressure the foot is subjected to under normal conditions. In this embodiment, it is possible to determine points of excess pressure along all surfaces of the foot and ankle as opposed to only the bottom or sole of the foot. In this embodiment, the pressure points could also be determined under more extreme conditions, such as those related to jogging, running, or rapid changes in momentum directions, such as those related to playing sports.

Whether the device being coated with the PSP is a sock or other device, the device should be fitted to the patient's foot in some manner to provide at least general reference points that enable corresponding points on the sock or other device to points on the foot once the foot is removed from the sock or other device. Such fitting methods will be readily apparent to one skilled in the art and could include, for example, applying a transferable dye to the inner surface of the sock. Further, while the thickness of the pressure-sensitive film is not a limitation on the oxygen-sensitive photoluminescence of the film, it is desirable that the film covering at least a portion of a sock be of a thickness that would not substantially interfere with the ability of the patient to comfortably wear the sock or the ability of the patient to wear the sock in conjunction with another foot covering, such as a shoe. Such thicknesses would be readily apparent to one of ordinary skill in the art.

In another aspect of the present invention is contemplated a pressure-sensitive film for use in evaluating pressure distribution across a surface that is capable of being tailored to specific use parameters. As the PSP-coated sock is used to detect areas of increased pressure on the foot, pressure quantification would not be expected to be the same for a 150-pound patient as for a 300-pound patient. Thus, it would be useful to have multiple PSP formulations for use with patients in different weight ranges or have a single PSP formulation designed to react differently within specific weight ranges. For example, the PSP of the present invention can be formulated for use throughout a specified weight range, such as, for example, 100 to 150-pounds patients. This could be achieved through alterations in the makeup of the polymer matrix such that oxygen diffuses in and out of the matrix more or less easily. Alternately, the PSP can be formulated with a probe molecule that is more or less oxygen-sensitive than other possible probe molecules. In this manner, it is possible to make a series of PSP formulations for use in analyzing pressure distributions, wherein each particular PSP, while effective over a broad patient weight range, shows maximum effectiveness and sensitivity over a more narrow weight range.

According to one specific PSP formulation, 7 mg of platinum tetrakis (pentafluorophenyl) porphine (PtTFPP) is dissolved in 11.3 g of polysiloxane with 3 g aluminum oxide. Such formulation is sensitive in the pressure range of about 270 psi to about 360 psi (about 5 kgf/cm$^2$ to about 25 kgf/cm$^2$), which would be expected to be useful for patients having a weight ranging from about 50 kg (about 110 lbs) to about 120 kg (about 265 lbs).

Another example of manipulating PSP formulation to achieve specific benefits could include preparing a single PSP that maintains maximum effectiveness over a broad range. Such could be achieved, for example, by using a single binder, or mixture of binders, in which multiple types of probe molecules are suspended. The probe molecules could be chosen according to their respective oxygen-sensitivity and their characteristic color of luminescence. A PSP prepared in this manner could have probe molecules that are only activated in one weight range and provide a distinctive emission spectra and also have probe molecules that are only activated in a different weight range and also provide a distinctive emission spectra that is different from the first probe. Similar results could also be achieved by varying the wavelength of the excitation spectra. In this embodiment, the PSP could have multiple probe molecules that each show maximum effectiveness at given weight ranges but also have emission spectra that overlap, which could be a source of interference. By knowing which probe is most effective at a given weight range, the weight of the patient, and the wavelength of light that will excite only that probe molecule associated with the given weight range, the correct excitation energy can be applied resulting in only one emission spectra, the one corresponding to the probe molecule that is most effective at the given weight range. In this manner, only one PSP need be formulated and the tailoring can be done at the detection phase by altering the wavelength of the excitation light.

In another embodiment of the present invention for use in detecting pressure distribution across the surface, the pressure-sensitive film can be used for covering at least a portion of a structure having an outer surface. According to this embodiment, the structure could be any structure capable of withstanding the weight of an adult patient and capable of substantially conforming to at least a portion of the foot of the patient. It is further contemplated by this embodiment that the pressure-sensitive film, while conforming to the shape of the foot, would not be in direct contact with the skin on the patient's foot. For example, the film can be applied to the outer surface of a sock, and then the patient allowed to wear the sock for a period of time. Another example could include applying the film to the outer surface of a shoe insole. The insole could be shaped to substantially conform to the shape of the patient's foot, and the insole coated with the pressure-sensitive film could be placed into the patient's shoe. The patient could then be allowed to wear the shoe for a period of time and the insole removed for examination. While wearing the shoe with the insole coated with the pressure-sensitive film, the patient could also be wearing another covering on the foot, such as a conventional, uncoated sock, that would not substantially interfere with the ability of the pressure-sensitive film on the insole to detect pressure points but would serve to keep the film from coming into direct contact with the skin of the patient's foot.

In another embodiment, the pressure-sensitive film could be applied to a structure that is designed to remain substantially stationary. In this embodiment, the film could be covering at least a portion of the substantially stationary structure and the patient could then be allowed to stand on the pressure-sensitive film on the structure for a period of time. The patient could then step off of the structure and the film could be removed for analysis. Also encompassed by this embodiment would be the use of a substantially stationary structure that included a removable pad. The word "pad" here is meant to describe a device that is firm yet somewhat deformable under pressure. One example of a "pad" as used herein could be a section of foam contained within a covering made of natural or synthetic material, such that when compressed, it would substantially conform to the shape of the foot exerting the pressure yet return to its previous shape upon removal of the external pressure. Another example could be a firm, yet somewhat deformable polymer, such as a silica gel, enclosed within a non-permeable membrane. The pressure-sensitive film could be coated onto the pad, the pad placed onto the substantially stationary structure, and the patient allowed to stand on the film-coated pad for a period of time. The pad could then be removed for pressure point analysis. When used in this manner, the same pad could be discarded after a single use or used repeatedly. If used repeatedly, the film could be reapplied intermittently.

In another aspect of the present invention, there is provided a sock for detecting pressure points on a foot of a patient, wherein the sock has a coloring agent or dye applied to at least a portion of the interior surface of the sock so that when the patient wears the sock, the coating material transfers from the interior surface of the sock to the foot at the pressure points. As used herein, the terms "coloring agent" and "dye" are intended to mean those materials that can move from or be transferred from the sock to the foot to indicate a pressure point. The terms "coloring agent" and "dye" are used collectively as "coloring material." At least a portion of the interior surface of the sock is coated with a coloring agent or dye such that when the patient's foot wears the sock, the coloring agent or dye transfers from the interior surface of the device to the foot at the pressure points as a detectable marking. The amount of the coating material transferred is determined by the pressure the foot exerts on the interior surface of the sock. Preferably, the amount of transfer under normal ordinary non-harmful low pressure is sufficiently different from the pressure exerted under harmful, ulceration-causing pressure. Most preferably, the transfer of the coating material is only detectable when the pressure is excessive.

Many removable coating materials can be used to achieve the above goals, as will be apparent to a skilled artisan in the chemical art. The materials should not cause any substantial adverse effect to the foot and the sock of this invention. One embodiment of the coating material for use in the socks of this invention is in the form of a powder. However, preferably, the coating material is in a paste-like form. The coating material includes, e.g., zinc oxide, titanium dioxide, or magnesium oxide and the like. When a paste containing the coating material is desired, non-toxic oils, glycerin, glycols, Vaseline, and the like can be mixed with the solid materials. An example of the coating material may be a paste composition including an oil (animal, vegetable, or mineral oils) of glyceride in admixture with a coloring agent powder or a powder of zinc oxide, titanium dioxide, or magnesium oxide and the like. For example, the paste can be made of about 1 to about 2.5 parts of glyceride and about 1–5 parts of the above powder blended together.

In another embodiment of the present invention, the coating material includes a coloring agent such as food coloring agents, water-soluble dyes, dyes soluble in an organic solvent (e.g., oil), and fluorescent dyes, and a suitable thickening agent in admixture. The coating material formulation may also include a liquid glycol such as ethylene glycol, propylene glycol, glycerin, polyethylene glycol, or the like.

The coating materials can be applied to the interior surface of the device by any suitable methods. Preferably, in the case of a paste, it can be applied as a spray and then allowed to dry. For example, the paste can be loaded into a conventional aerosol spray can with a suitable propellant such as butane. The paste can be applied to the device by spraying the coating materials from the aerosol to the interior surface of the device. Optionally, the applied coating material becomes substantially dry after the application. In a preferred embodiment, conventional denture indicator pastes such as Hydrent® denture indicator paste and Occlude® aerosol indicator marking spray, both of which are commercially available from Pascal Co. Inc., Bellevue, Wash., are used.

In a preferred embodiment, the device comprises a sock having a coating material applied to at least a portion of the interior surface of the sock. The sock can be any conventional sock made of any textile or non-textile materials. In a preferred embodiment of the invention, there is provided a sock having at least two layers and most preferably, the sock is a double-layered sock. The inner layer is impregnated or coated with a dye that is in a non-acidic state and changes color when it becomes acidic. The outer sock layer contains an acid such as, for example, citric acid. When pressure is applied to the dye containing area in the sock, pressure is applied against both layers of the sock and the dye is caused to react with the acid and changes colors when the dye turns acidic, thereby indicating a pressure point. In another embodiment of the invention, the dye may be contained on a pressure-sensitive film and adhered to the interior of the sock. In another preferred embodiment, the acid is in a microencapsulated form. In such a form, the acid is contained in microcapsules that retain their integrity, thus keeping the acid away from the dye, until pressure is applied to the microcapsules. When pressure is applied, the microcapsules are breached, releasing the acid to interact with the dye. In this embodiment, it is envisioned that the micro capsules can be prepared such that they will only release the acid within the micro capsules when placed under excessive pressure, such as the pressure exerted on the pressure points of the foot.

The sock of this invention can be useful in detecting pressure points of a patient's foot with diminished sensation. Therefore, the present invention is useful in diagnosing and treating patients with sensory neuropathy. The term "neuropathy" is generally used to denote functional disturbances and/or pathological changes in the peripheral nervous system. There are multiple known causes of peripheral neuropathy, including infection, heredity, trauma and entrapment, cold, toxins, certain drugs, deficiency of certain vitamins (such as $B_{12}$), radiation, severe illness, gland and kidney diseases, some cancers, immune system abnormalities and inflammation. Examples of specific diseases known to result in neuropathies include leprosy, diabetes, thyroid disease, and HIV/AIDS. The present invention is useful for patients suffering from neuropathies due to any of the above causes, and is especially useful in diabetic patients. With neuropathic foot disease, patients often lack sufficient sensation to feel excess pressure on the feet. Such excessive pressure is often exerted by improperly fitted shoes, or is because of abnormal growth of tissue in the feet. If the excessive pressure continues, foot sores or ulceration can develop and aggravate due to continued excessive pressure or rubbing. Prolonged suffering from these problems can lead to the necessity of amputation.

With the present invention, for example, the sock having the coated materials applied onto the interior surface thereof is worn on a patient's foot, which is diagnosed of, or suspected of, diminished sensation. The sock is worn just like a normal sock and thus does not interfere with the patient's normal life. For a period of time, which can be as short as 10 minutes to 30 minutes, depending upon which dye is used, up to a longer time, such as from one to several days. After that time, the sock is removed from the foot and both the foot and the sock are examined. The transfer of the coating material to the foot is usually associated with high pressure points. Thus, by examining the sock and the foot, high pressure points can be determined. Accordingly, the high pressure points can be treated with suitable medicines or devices to inhibit or prevent sores or ulceration. Alternatively, the shoes of the patient can be altered based on the location of the high pressure points to better fit the foot.

Experimental

The present invention is more fully illustrated by the following examples, which are set forth to illustrate the present invention and are not to be construed as limiting thereof.

EXAMPLE 1

PSP Formulation

The polymer matrix binder was prepared first by dissolving 48.9 mg (0.22 mmol) methyltriacetoxysilane and 500 mg (0.056 mmol of Si—OH end groups) silanol-terminated polydimethylsiloxane in 4 ml methylene chloride ($CH_2Cl_2$) and stirring for 0.5 h. To the binder solution was added 1 mg platinum octaethylporphyrin, which was followed by 5 min. stirring and the addition of two drops glacial acetic acid.

EXAMPLE 2

PSP Formulation with Inorganic Binder 11.3 g of polysiloxane (SR-900 purchased form GE Silicones, Pittsfield, Mass.) was dissolved in toluene to produce a 50% (v/v) silicone polymer solution. 7 mg of platinum tetrakis (pentafluorophenyl) porphine (purchased from Porphyrin Products, Logan, Utah) was added. The mixture was further dissolved in 36 ml of p-chlorotrifluorotoluene (Oxsol-100 purchased from Occidental Chemical Corp., Dallas, Tex.). Aluminum oxide ($Al_2O_3$) was then added at an amount of 1.5, 3.0, 3.5, 4.0, or 4.5 g (depending upon the desired PVC). The mixture was ball-milled at room temperature for 2 hr. to produce the resultant PSP.

Many modifications and other embodiments of the invention will come to mind to one skilled in the art to which this invention pertains having the benefit of the teachings presented in the foregoing descriptions. Therefore, it is to be understood that the invention is not to be limited to the specific embodiments disclosed herein and that modifications and other embodiments are intended to be included within the scope of the appended claims. Although specific terms are employed herein, they are used in a generic and descriptive sense only and not for purposes of limitation.

That which is claimed:

1. A sock for detecting pressure points on a foot comprising:
   a sock having an inner and an outer surface; and a pressure-sensitive film applied to at least a portion of the inner surface or outer surface of said sock, wherein said film comprises an oxygen permeable polymer matrix and oxygen-sensitive photo luminescent probe molecules dispersed within said matrix.

2. The sock of claim 1, wherein the oxygen permeable polymer matrix comprises at least one polymer selected from the group consisting of silicone-based polymers, siloxane-based polymers, and mixtures thereof.

3. The sock of claim 2, wherein the oxygen permeable polymer matrix comprises polydimethylsiloxane.

4. The sock of claim 1, wherein the oxygen-sensitive photo luminescent probe is selected from the group consisting of platinum octaethylporphyrin, palladium octaethylporphyrin, platinum tetra(pentafluorophenyl)porphyrin, palladium tetra(pentafluorophenyl)porphyrin, platinum tetraphenylporphyrin, palladium tetraphenylporphyrin, platinum octaethylporphyrin ketone, palladium octaethylporphyrin ketone, tris(2,2'-bipyridine)ruthenium(II) chloride pentahydrate, platinum tetrabenzoporphyrin, palladium tetrabenzoporphyrin, complexes of ruthenium (II), osmium (II), iridium (III), rhodium, rhenium, or chromium (III) with 2,2'-bipyridine, 1,10-phenanthroline, 4,7-diphenyl(1,10-phenanthroline), 4,7-dimethyl-1,10-phenanthroline, 4,7-disulfonated-diphenyl-1,10-phenanthroline, 2,2'-bi-2-thiazoline, 2,2'-bithiazole, 5-bromo-1,10-phenanthroline, or 5-chloro-1,10-phenanthroline, and mixtures thereof.

5. The sock of claim 4, wherein the oxygen-sensitive photo-luminescent probe is platinum octaethylporphyrin.

6. The sock of claim 1, wherein the pressure-sensitive film further comprises at least one inorganic pigment selected from the group consisting of aluminum oxide, iron oxide, lead oxide, chrome oxide, zinc phosphate, titanium dioxide, cadmium, ultramarine, zinc sulfide, barium sulfate, molybdate, and mixtures thereof.

7. The sock of claim 6, wherein the inorganic pigment is aluminum oxide.

8. The sock of claim 1, wherein the pressure-sensitive film comprises polydimethylsiloxane and platinum octaethylporphyrin.

9. The sock of claim 8, wherein the pressure-sensitive film further comprises aluminum oxide.

10. A method for detecting pressure points on a foot of a patient comprising:
    providing a sock having an inner and an outer surface and having a pressure-sensitive film applied to at least a portion of the inner surface or outer surface, wherein said film comprises an oxygen permeable polymer matrix and oxygen-sensitive photo luminescent probe molecules dispersed within said matrix;
    fitting said sock to the foot of the patient;
    wearing said sock for a period of time;
    exposing said sock to an excitation energy source capable of exciting said probe molecules from the ground energy state to an excited energy state;
    detecting the energy released by said probe molecules when they return from said excited energy state to said ground energy state; and
    determining the areas where the foot exerted the greatest pressure on the sock by comparing a map of the emission spectra with the film and the patient's foot.

11. The method of claim 10, wherein the oxygen permeable polymer matrix comprises at least one polymer selected from the group consisting of silicone-based polymers, siloxane-based polymers, and mixtures thereof.

12. The method of claim 11, wherein the oxygen permeable polymer matrix comprises polydimethylsiloxane.

13. The method of claim 10, wherein the oxygen-sensitive photo luminescent probe is selected from the group consisting of platinum octaethylporphyrin, palladium octaethylporphyrin, platinum tetra(pentafluorophenyl)porphyrin, palladium tetra(pentafluorophenyl)porphyrin, platinum tetraphenylporphyrin, palladium tetraphenylporphyrin, platinum octaethylporphyrin ketone, palladium octaethylporphyrin ketone, tris(2,2'-bipyridine)ruthenium(II) chloride pentahydrate, platinum tetrabenzoporphyrin, palladium tetrabenzoporphyrin, complexes of ruthenium (II), osmium (II), iridium (III), rhodium, rhenium, or chromium (III) with 2,2'-bipyridine, 1,10-phenanthroline, 4,7-diphenyl(1,10-phenanthroline), 4,7-dimethyl-1,10-phenanthroline, 4,7-disulfonated-diphenyl-1,10-phenanthroline, 2,2'-bi-2-thiazoline, 2,2'-bithiazole, 5-bromo-1,10-phenanthroline, or 5-chloro-1,10-phenanthroline, and mixtures thereof.

14. The method of claim 13, wherein the oxygen-sensitive photo-luminescent probe is platinum octaethylporphyrin.

15. The method of claim 10, wherein the pressure-sensitive film further comprises at least one inorganic pigment selected from the group consisting of aluminum oxide, iron oxide, lead oxide, chrome oxide, zinc phosphate, titanium dioxide, cadmium, ultramarine, zinc sulfide, barium sulfate, molybdate, and mixtures thereof.

16. The method of claim 15, wherein the inorganic pigment is aluminum oxide.

17. The method of claim 10, wherein said excitation energy source comprises an ultraviolet light source.

18. The method of claim 10, wherein said excitation energy source provides excitation energy at a wavelength of about 200 nm to about 600 nm.

19. The method of claim 18, wherein said excitation energy is at a wavelength of about 390 nm.

20. The method of claim 10, wherein said detecting step further comprises using a cooled, 14-bit charge-coupled device camera.

21. A method of diagnosing potential areas for the development of plantar ulcers comprising:
    providing a pressure-sensitive film for detecting pressure distribution across a surface when subjected to a load, said film comprising an oxygen permeable polymer matrix and oxygen-sensitive photo luminescent probe molecules dispersed within said polymer matrix;
    subjecting the film to foot pressure exerted by a patient;
    exposing the film to an excitation energy source capable of exciting the probe molecules from the ground energy state to an excited energy state;
    detecting the energy released by the probe molecules when they return from the excited energy state to the ground energy state; and
    determining the areas where the foot exerted the greatest pressure on the surface of the film by comparing a map of the emission spectra with the film and the patient's foot.

22. The method of claim 21, wherein the oxygen permeable polymer matrix comprises at least one polymer selected from the group consisting of silicone-based polymers, siloxane-based polymers, and mixtures thereof.

23. The method of claim 22, wherein the oxygen permeable polymer matrix comprises polydimethylsiloxane.

24. The method of claim 21, wherein the oxygen-sensitive photo luminescent probe is selected from the group consisting of platinum octaethylporphyrin, palladium octaethylporphyrin, platinum tetra(pentafluorophenyl) porphyrin, palladium tetra(pentafluorophenyl)porphyrin, platinum tetraphenylporphyrin, palladium tetraphenylporphyrin, platinum octaethylporphyrin ketone, palladium octaethylporphyrin ketone, tris(2,2'-bipyridine) ruthenium(II) chloride pentahydrate, platinum tetrabenzoporphyrin, palladium tetrabenzoporphyrin, complexes of ruthenium (II), osmium (II), iridium (III), rhodium, rhenium, or chromium (III) with 2,2'-bipyridine, 1,10-phenanthroline, 4,7-diphenyl(1,10-phenanthroline), 4,7-dimethyl-1,10-phenanthroline, 4,7-disulfonated-diphenyl-1,10-phenanthroline, 2,2'-bi-2-thiazoline, 2,2'-bithiazole, 5-bromo-1,10-phenanthroline, or 5-chloro-1,10-phenanthroline, and mixtures thereof.

25. The method of claim 24, wherein the oxygen-sensitive photo-luminescent probe is platinum octaethylporphyrin.

26. The method of claim 21, wherein the pressure-sensitive film further comprises at least one inorganic pigment selected from the group consisting of aluminum oxide, iron oxide, lead oxide, chrome oxide, zinc phosphate, titanium dioxide, cadmium, ultramarine, zinc sulfide, barium sulfate, molybdate, and mixtures thereof.

27. The method of claim 26, wherein the inorganic pigment is aluminum oxide.

28. The method of claim 21, wherein said excitation energy source comprises an ultraviolet light source.

29. The method of claim 21, wherein said excitation energy source provides excitation energy at a wavelength of about 200 nm to about 600 nm.

30. The method of claim 29, wherein said excitation energy is at a wavelength of about 390 nm.

31. The method of claim 21, wherein said detecting step further comprises using a cooled, 14-bit charge-coupled device camera.

32. The method of claim 21, further comprising providing a sock with an inner surface and an outer surface, wherein the pressure-sensitive film is applied to at least a portion of the inner surface or the outer surface of the sock.

33. The method of claim 21, further comprising providing a shoe insole sized to correspond to the size of the patient's foot, wherein the pressure-sensitive film is applied to at least a portion of the insole, and placing the insole a shoe to be worn by the patient.

34. A sock for detecting pressure points on a foot comprising:
a sock having an inner and an outer surface; and a pressure-sensitive film applied to at least a portion of the inner surface or outer surface of said sock, wherein said film comprises an oxygen permeable polymer matrix, oxygen-sensitive photo luminescent probe molecules dispersed within said matrix, and at least one inorganic pigment.

* * * * *